United States Patent [19]
Blackman et al.

[11] Patent Number: 5,572,319
[45] Date of Patent: Nov. 5, 1996

[54] STAIN DETECTOR APPARATUS AND METHOD

[76] Inventors: Stephen E. Blackman, 1906 Westfield Ave., Scotch Plains, N.J. 07076; Daniel Eisen, 404 Brookside La., So. Somerville, N.J. 08876

[21] Appl. No.: 327,612

[22] Filed: Oct. 24, 1994

[51] Int. Cl.$^6$ .................................................. C01N 21/64
[52] U.S. Cl. ........................................ 356/238; 250/485.1
[58] Field of Search .................................. 356/429, 238; 362/125, 133, 154, 253; 250/461.1, 302, 485.1

[56] References Cited

U.S. PATENT DOCUMENTS 4,634,872  1/1987  Janus et al. .......................... 250/461.1

FOREIGN PATENT DOCUMENTS 298140  12/1988  Japan .

Primary Examiner—Richard A. Rosenberger
Attorney, Agent, or Firm—Ezra Sutton

[57] ABSTRACT

A stain detector is provided for detecting stains in a fabric which includes a housing having a fabric opening for receiving the fabric to be inspected and a viewing opening for inspecting the fabric; an incandescent lamp and a fluorescent lamp for projecting light rays toward the fabric opening; a U-shaped reflector mounted within the housing to reflect the light rays toward the fabric opening; and switches for activating the lamps prior to inspecting the fabric through the viewing opening.

3 Claims, 6 Drawing Sheets

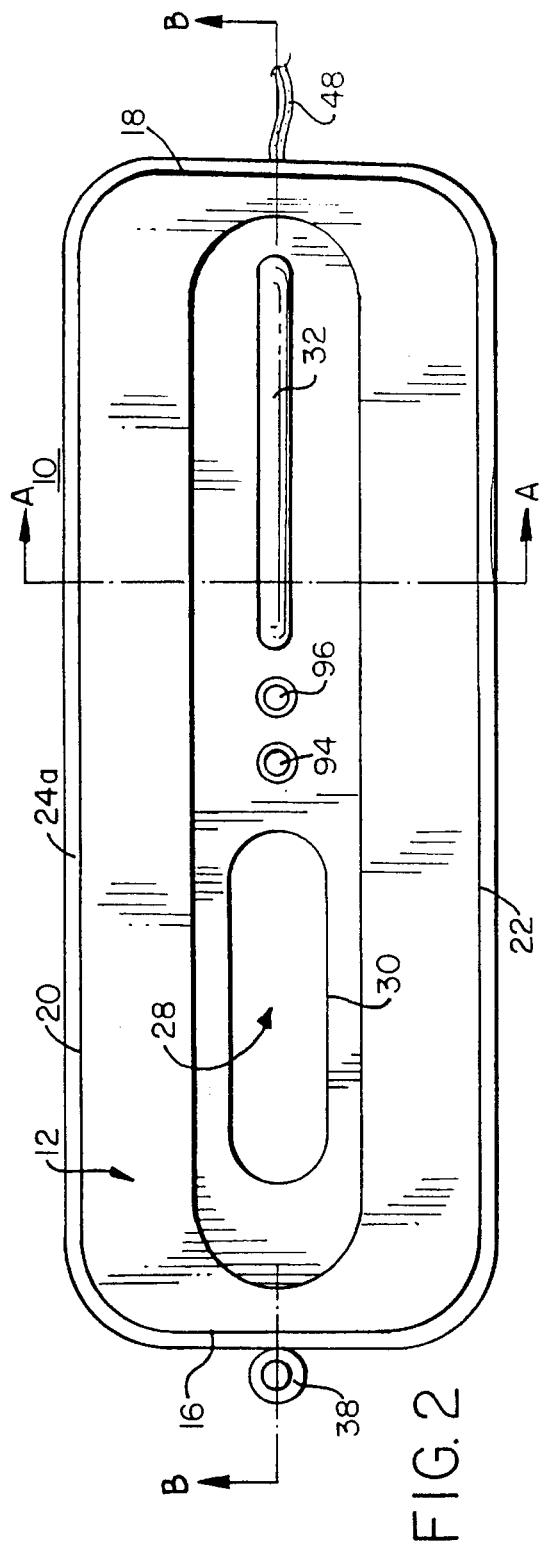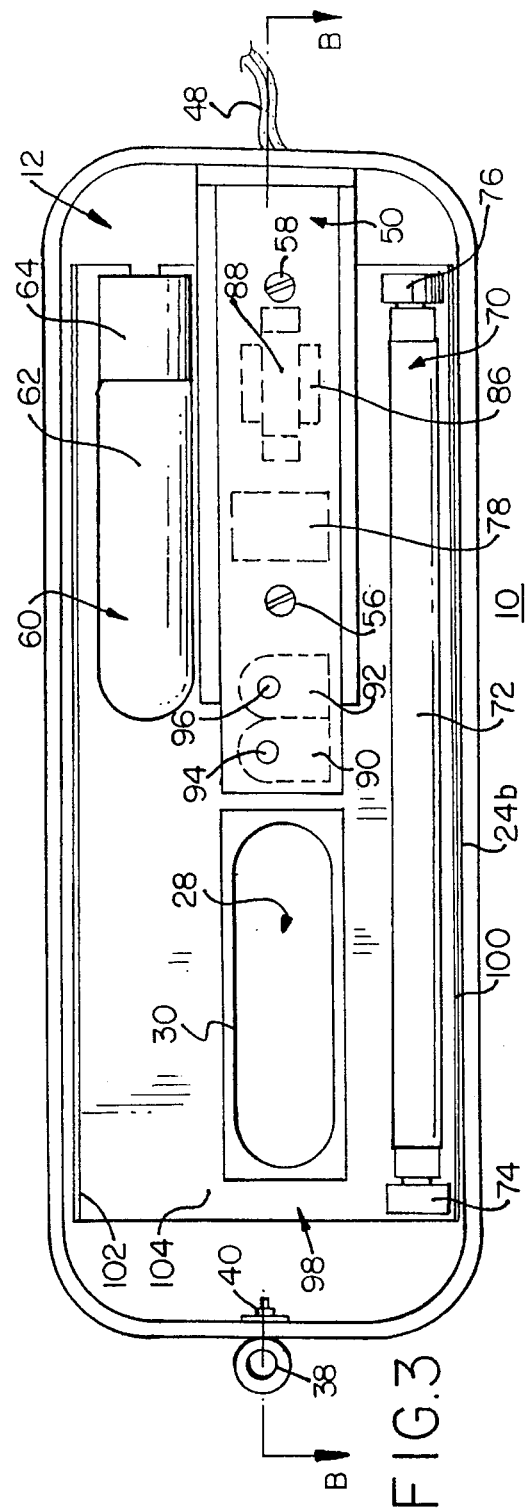

STAIN DETECTOR APPARATUS AND METHOD

FIELD OF THE INVENTION

This invention relates to a stain detector apparatus and method and, more particularly, to an apparatus and method for identifying the type of stain on a fabric and for identifying flaws in the fabric, such as snags, thread shifting, and weak areas.

BACKGROUND OF THE INVENTION

Dry cleaners often have a difficult time explaining to customers invisible stains, set stains, fabric flaws, fabric limitations, and other damage to garments, upholstery, and rugs to be cleaned. In the past, cleaners have used light to reveal stains in fabrics, to reveal fabric weak areas, and to identify stains within fabrics. The use of light for identifying stains and fabric flaws has been helpful to personnel in textiles, dry cleaners, garment analysts, museum curators, conservators, restorators, and manufacturers and retailers of clothing, textiles, and upholstered furniture. A stain detector apparatus would be useful to identify stains and flaws in fabrics.

DESCRIPTION OF THE PRIOR ART

U.S. Pat. No. 3,839,637 to A. Willis discloses an ultraviolet lamp, which transmits either ultraviolet or black light. This patent provides for the detecting of woven or knitted yarn which is impregnated with a material visible only when subjected to ultraviolet light, thus providing guidelines for cutting or measuring cloth.

The prior art patents do not disclose an apparatus and method for detecting fabric stains and/or flaws in fabrics. The prior art does not teach the use of an apparatus for stain detection having a housing with a fabric opening, a viewing opening, a handle, an incandescent lamp, a fluorescent lamp, and a light reflector for directing light rays to the fabric for inspection of stains.

Accordingly, an object of the present invention is to provide an apparatus that allows for stain detection and analysis of flawed or damaged fabrics in a quick and efficient manner.

Another object of the present invention is to provide a stain detector apparatus that is easy to use, lightweight, portable, convenient, and durable.

Another object of the present invention is to provide a stain detector apparatus that is useful to personnel in the areas of textiles, dry cleaners, garment analysts, museum curators, conservators, restorators, and manufacturers and retailers of clothing, textiles, and upholstered furniture.

Another object of the present invention is to provide a method for accurately identifying stains in various types of fabrics.

It is still another object of the present invention to provide a method for determining fabric defects in various types of fabric materials used in garments, upholstery, rugs, and the like.

A still further object of the present invention is to provide a stain detector and method of stain detection that utilizes the effects of light to study fabrics, dyes and stains.

An even further object of the present invention is to provide a stain detector and method of stain detection that will minimize claim submissions for improper cleaning of garments by the stain detector user.

A still further object of the present invention is to provide a stain detector apparatus that is portable, battery-operated, lightweight, compact, and hand held.

SUMMARY OF THE INVENTION

The present invention discloses a stain detector apparatus and a method for stain detection and fabric defect analysis using the effects of incandescent and fluorescent light rays to study fabrics, dyes, and stain compositions.

In the preferred or first embodiment, the stain detector apparatus includes a plastic housing having a fabric opening for receiving the fabric to be inspected and a viewing opening for inspecting the fabric for one or more stains. An incandescent lamp fixture and a fluorescent lamp fixture are mounted in the housing for projecting their respective light rays toward the fabric opening and onto the fabric to be inspected. Within the housing of the stain detector, there is a U-shaped light reflector having three integral sides which reflect the light rays toward the fabric opening and onto the fabric to be inspected. The stain detector has two activating switches for turning ON and OFF the incandescent and fluorescent lamp fixtures to inspect the fabric through the viewing opening. The stain detector of the first embodiment is powered by A.C. current. The stain detector housing can be made in any shape, such as rectangular, circular, or oval in shape.

In the second embodiment, the stain detector apparatus is a portable, hand-held version of the first embodiment, including a compact plastic housing having a fabric opening; a viewing opening; an incandescent lamp; a fluorescent lamp; a light reflector, and a storage compartment for batteries. The portable stain detector also has two switches which activate the incandescent and fluorescent light bulbs. This lightweight, portable, compact stain detector can be used in the field for inspecting fabrics in warehouses or trucks, or inspecting garments/textiles damaged from various staining sources, such as oil, dirt, and the like.

In the present invention, there is also provided a method of operating the first and second embodiments of the stain detector apparatus. The method of detecting and identifying stains on fabric using the stain detector includes the following steps:

a) placing the housing on the fabric to be inspected, such that the fabric opening of the housing faces the stain side of the fabric;

b) activating the fluorescent lamp fixture and directing the ultraviolet light rays toward the fabric opening and the stain side of the fabric;

c) inspecting the stain side of the fabric through the viewing opening to determine if a stain is present;

d) identifying the type of stain by the type of reaction the ultraviolet rays have on the stain;

e) placing the housing on the fabric to be inspected, such that the fabric opening of the housing faces the other side of the fabric opposite to the stain side;

f) activating the incandescent lamp fixture and directing the incandescent light rays toward the fabric opening and the other side of the fabric;

g) inspecting the fabric from the stain side of the fabric through the viewing opening to determine if a stain is present; and h) identifying the type of stain by the type of reaction the incandescent light rays have on the stain.

The identification of the type of stain detected on the fabric and a method recommended for the cleaning and removal of that stain is simplified and made easy by the use of a stain detection analysis chart.

BRIEF DESCRIPTION OF THE DRAWINGS

Further objects, features, and advantages of the present invention will become apparent upon consideration of the detailed description of the presently-preferred embodiments, when taken in conjunction with the accompanying drawings, wherein:

FIG. 2 is a top plan view of the first embodiment of the present invention showing the viewing opening, switches, and handle;

FIG. 3 is a bottom plan view of the first embodiment of the present invention showing the fabric opening, the viewing opening, the incandescent lamp, and the fluorescent lamp;

DETAILED DESCRIPTION OF THE PREFERRED EMBODIMENTS

Figure 1A:
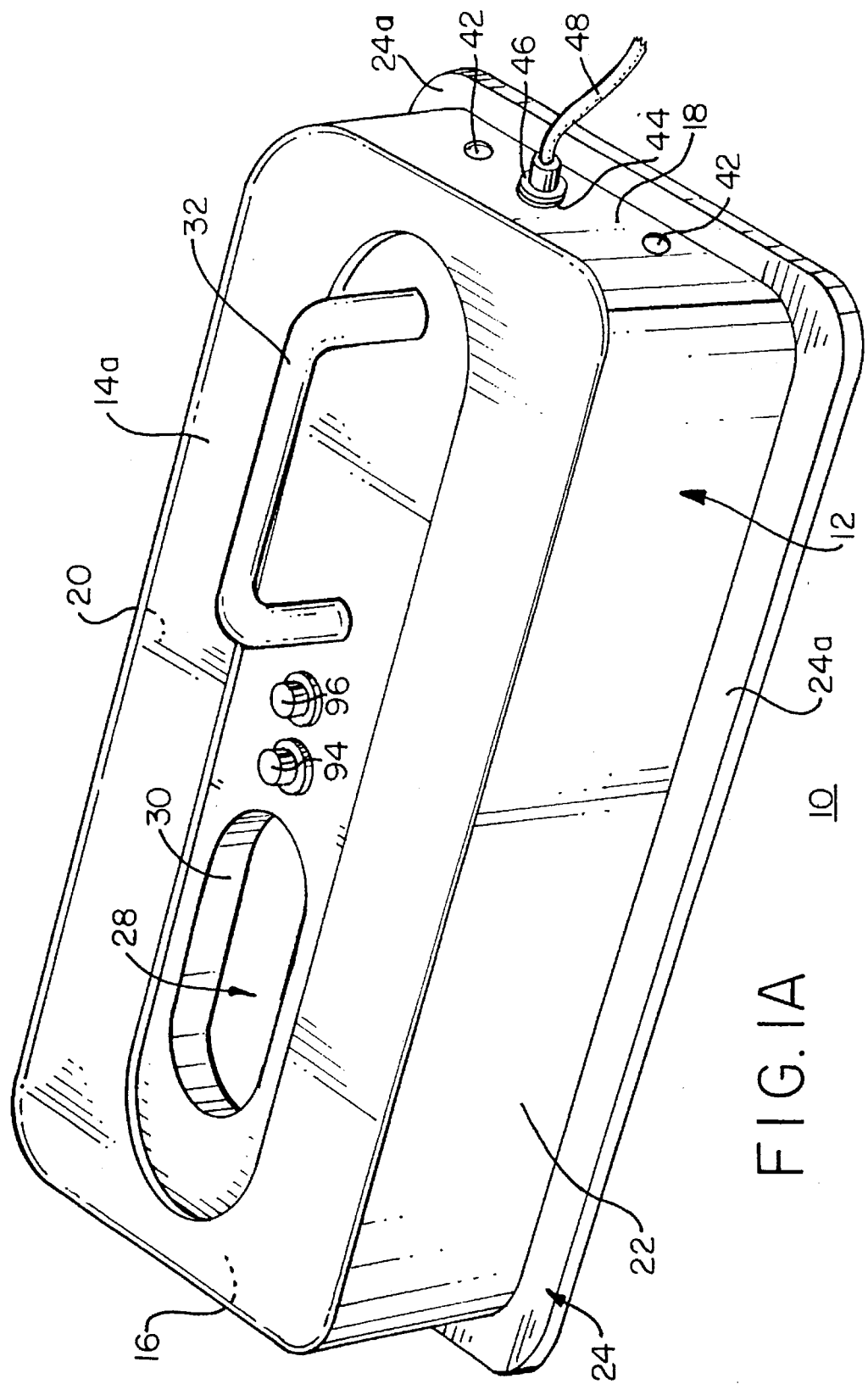
FIG. 1A is a perspective frontal view of the first embodiment of the present invention showing the stain detector apparatus.
Figure 1B:
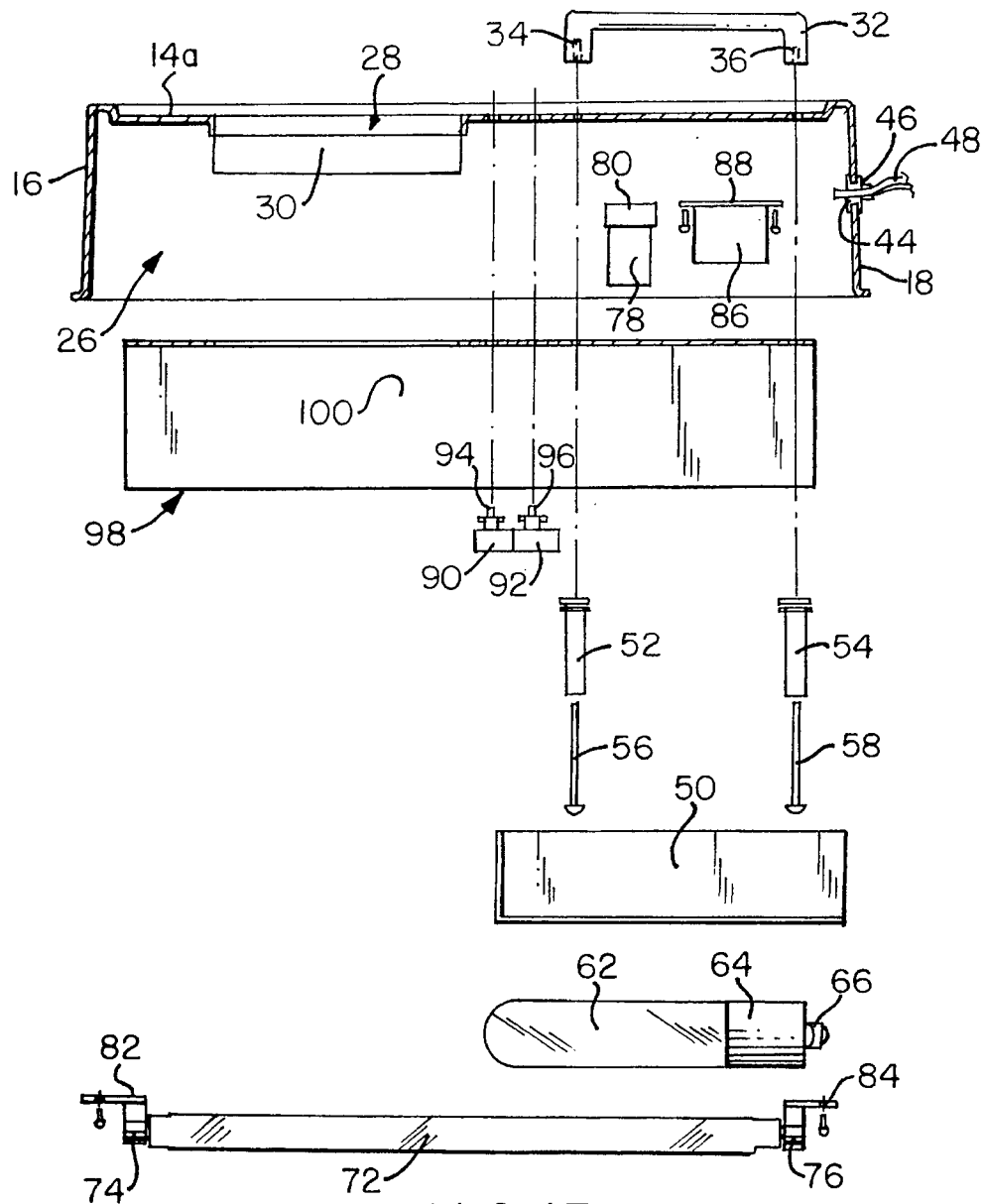
FIG. 1B is an exploded view of the first embodiment of the present invention showing sectional views of the primary component parts of the stain detector.

FIGS. 1A and 1B show the first embodiment of the present invention. The stain detector apparatus assembly 10 includes a housing 12 having a fabric opening 26, a viewing opening 28, a handle 32, a hanging hook 38, a vent opening 42, an electrical cord opening 44, and switches 94 and 96. Within the housing 12, as depicted in FIGS. 1B to 6, there is an electrical box 50, an incandescent lamp fixture 60, a fluorescent lamp fixture 70, and a light reflector 98. As used herein, it should be understood that the term "stain" includes stains, soiling, and flaws in fabrics.

As shown in FIGS. 1A and 1B, the stain detector apparatus 10 includes a rectangular, plastic housing 12 having a top wall 14, sidewalls 16, 18, 20, and 22, and a bottom perimeter edge 24, which defines the fabric opening 26. The oval viewing opening 28 has an oval perimeter sidewall 30. The viewing opening 28, switches 94 and 96, and handle 32 are centrally positioned along the axis line B—B, as depicted in FIG. 2. The handle 32 enables the user or operator to move the stain detector 10 in a vertical or horizontal motion when examining a fabric or garment for stains. The handle 32, having threaded openings 34 and 36, is mounted on top wall surface 14a by threaded screw bolts 56 and 58.

Figure 5:
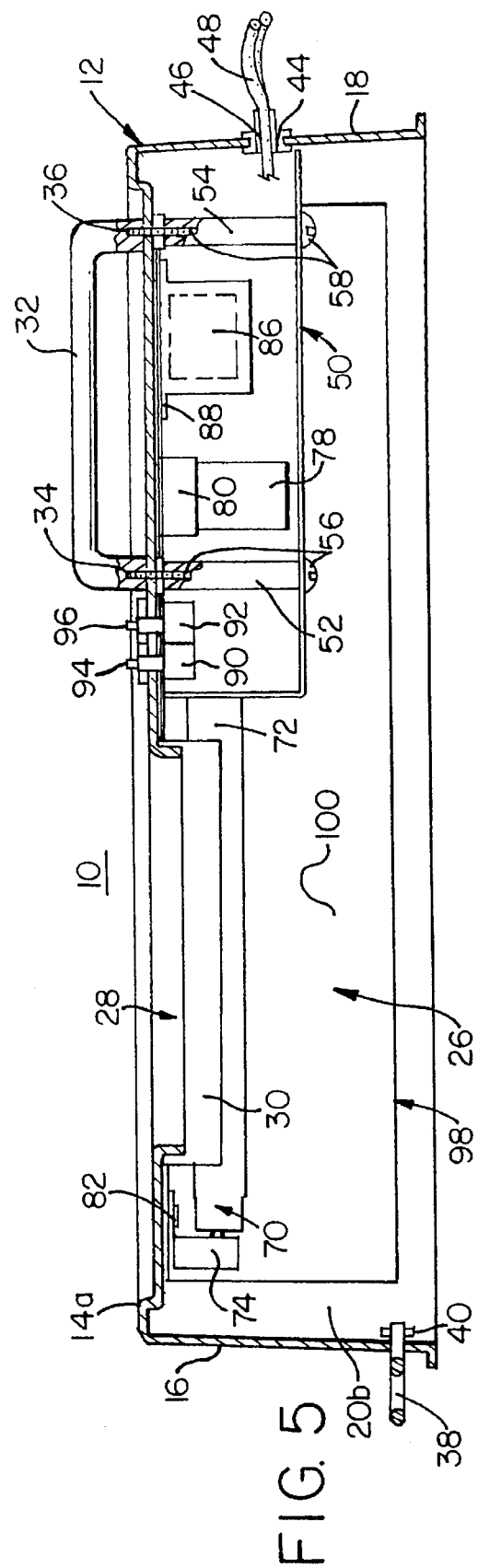
FIG. 5 is a side sectional view of the first embodiment of the present invention taken along the sectional line B—B of FIG. 2 showing the fluorescent lamp, a viewing opening, an electrical box with component parts therein, a light reflector, and a handle.

The hanging hook 38 is located on sidewall 16 and is centrally positioned near the bottom perimeter edge 24a, as depicted in FIGS. 2, 3, and 5. The hanging hook 38 is attached to side wall 16 by a connecting device 40. The vent opening 42 is used for heat dissipation and is located on sidewall 18. Electrical cord opening 44 includes a grommet 46 through which the electrical cord 48 passes. The electrical cord 48 extends outwardly from cord opening 44 and is centrally positioned on sidewall 18.

As shown in FIGS. 1B and 3 to 6, the interior components of housing 12 include the incandescent lamp fixture 60 having an incandescent light bulb 62, which is received in a porcelain lamp socket 64 and is attached to top wall inner surface 14b by a connecting device 66. Housing 12 also includes the fluorescent lamp fixture 70 having a fluorescent light bulb 72, which is received in miniature sockets 74 and 76 and is attached to the top interior reflector surface 102 by socket connectors 82 and 84. The fluorescent lamp fixture 70 also has a fluorescent lamp starter 78, a starter base 80, and a fluorescent lamp transformer 86 attached to top interior reflector surface 102 by connector 88.

The incandescent light source 60 provides white visible light, and any lamps may be used to provide such light rays, including a fluorescent fixture having a fluorescent light bulb that provides white visible light. In addition, the fluorescent light source may be a fluorescent bulb, a black light bulb, a black light/blue light bulb, or an infrared light bulb.

The electrical box 50 is located within housing 12, as shown in FIGS. 1B and 3 to 5 and includes the switch circuits 90 and 92 for the incandescent and fluorescent lamp fixtures 60 and 70; the fluorescent lamp starter 78 and starter base 80; and the fluorescent transformer 86. The electrical box 50 is held in place by sleeves 52 and 54 and handle screw bolts 56 and 58, which are received into the handle thread openings 34 and 36 of handle 32. The electrical box 50 is centrally positioned along the B—B axis line and adjacent to sidewall 18 within housing 12, as depicted in FIG. 3.

Figure 1C:
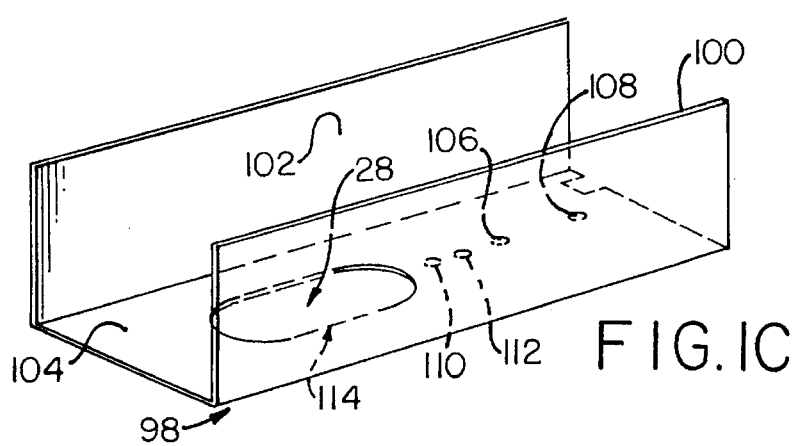
FIG. 1C is a perspective bottom view of the first embodiment of the present invention showing the light reflector and the viewing opening.
Figure 4:
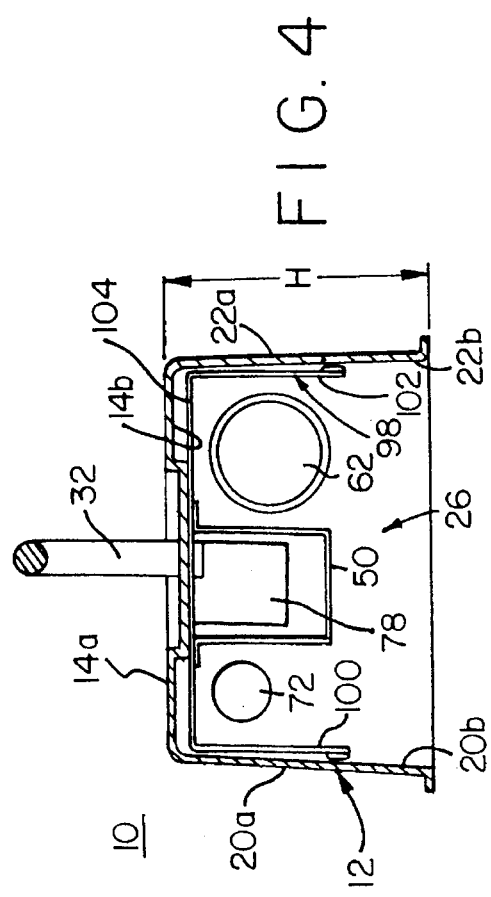
FIG. 4 is a side sectional view of the first embodiment of the present invention taken along the sectional line A—A of FIG. 2 showing the incandescent and fluorescent lamps, a light reflector, an electrical box, a handle, and a fabric opening.

As shown in FIGS. 1B, 1C, and 3 to 5, light reflector 98 is U-shaped and has integrally attached reflecting sidewalls 100 and 102 and a light reflecting top wall 104 and is located within the interior space of housing 12. Light reflector 98 is held in place by handle screw bolts 56 and 58 through hole openings 106 and 108 in which screw bolts 56 and 58 are attached to the threaded handle openings 34 and 36 of handle 32. The U-shaped light reflector 98 is positioned within housing 12, such that exterior sidewalls 100 and 102 and exterior top wall 104 are adjacent to interior sidewalls 20b and 22b and interior top wall 14b of housing 12, respectively, as depicted in FIGS. 1C, 4, and 5. The inner light reflecting surfaces of reflector 98 can be made of any highly-reflective surface, such as highly-polished reflective metal, a silverized plastic, a painted reflective finish, a coated metallic reflective material, or a mirror surface. The light reflector 98 has an oval opening 114 corresponding to the viewing opening 28 and has switch openings 110 and 112 for the switch activating components 94 and 96.

The stain detector apparatus 10 has a length of approximately 13¾ inches, a width of approximately 5½ inches, and a height of approximately 3½ inches. The housing 12 wall thickness is approximately ⅛ of an inch. The oval viewing opening has dimensional measurements of approximately 4½ inches in length and approximately 1 inch in width. The rectangular fabric opening has a dimensional area measurement of approximately 75 square inches.

Figure 6:
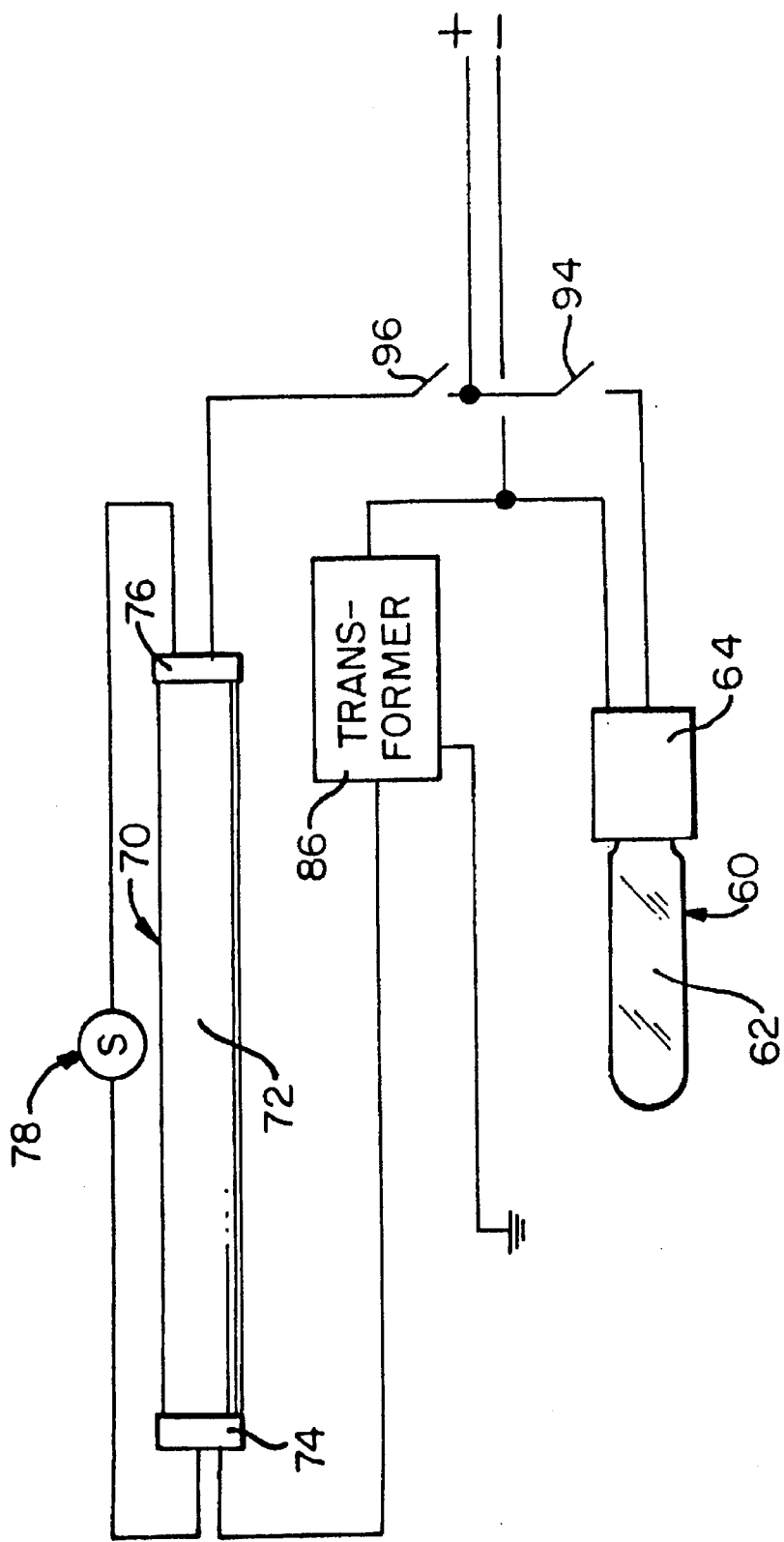
FIG. 6 is a schematic diagram of the first embodiment of the present invention showing the electrical circuit.

As shown in FIG. 6, in the electrical circuitry, the incandescent lamp fixture 60 is connected to switch 94, and the fluorescent lamp fixture 70 is connected to transformer 86 and to switch 96. Switches 94 and 96 are connected to the power source, which may be an A.C. source or a battery pack.

The incandescent light bulb 62 of fixture 60 is a standard, commercially manufactured 20, 40, or 60-watt frosted light bulb, and the fluorescent light bulb 72 of fixture 70 is a standard 8-watt ultraviolet light bulb.

Figure 7:
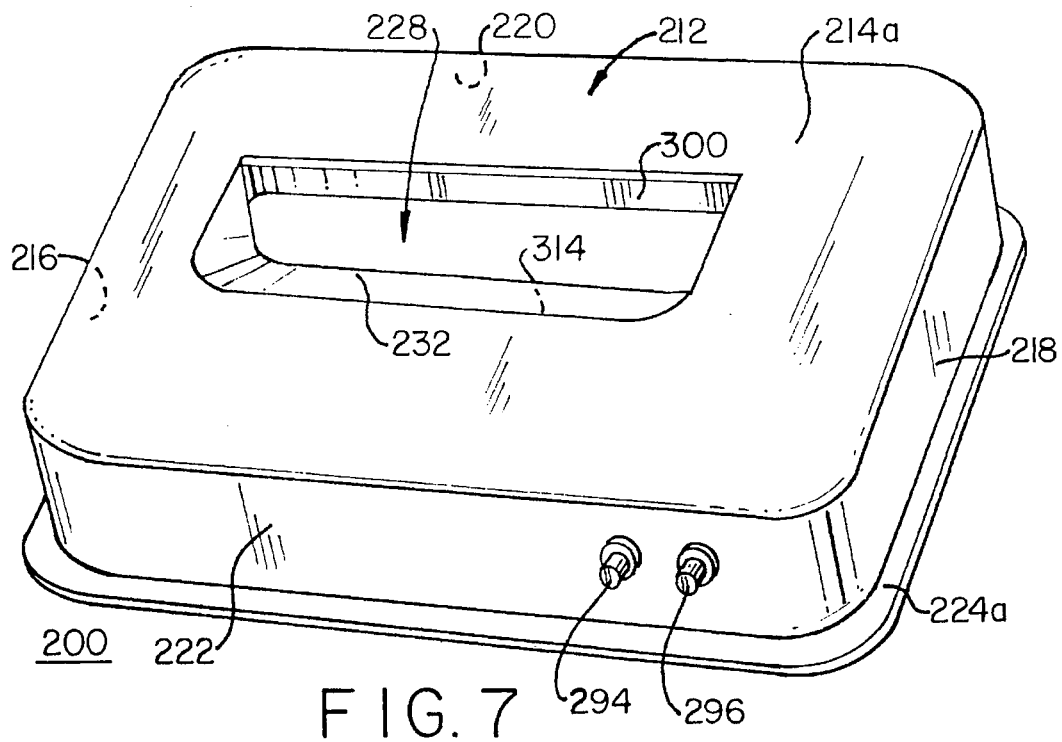
FIG. 7 is a perspective frontal view of the second embodiment of the present invention showing the hand-held, portable stain detector apparatus.
Figure 8:
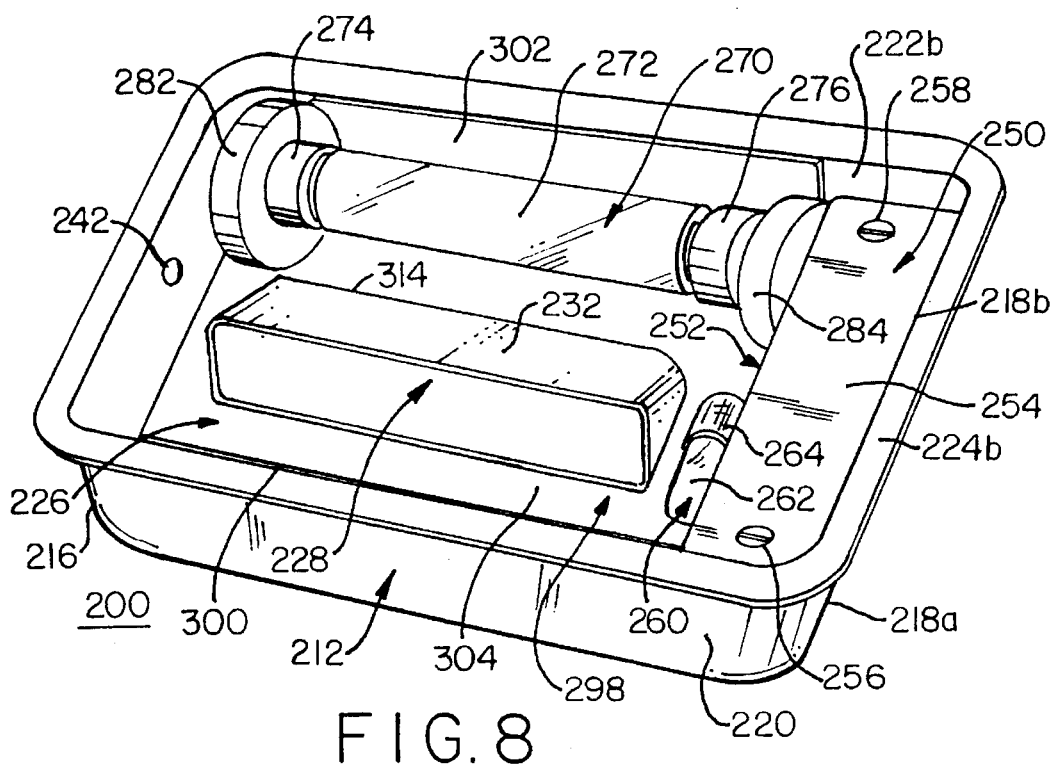
FIG. 8 is a perspective bottom view of the second embodiment of the present invention showing the hand-held, portable stain detector apparatus and its primary component parts.

As shown in FIGS. 7 and 8, there is a second embodiment of the present invention. The hand-held, portable stain detector apparatus 200 includes a housing 212 having a fabric opening 226, a viewing opening 228, a vent opening 242, and switches 294 and 296. Within the housing 212, as depicted in FIG. 8, there is an electrical and battery storage compartment 250, an incandescent lamp fixture 260, a fluorescent lamp fixture 270, and a metallic light reflector 298. The portable stain detector apparatus 200 includes a lightweight rectangular plastic housing 212 having a top wall 214, sidewalls 216, 218, 220, and 222, and a bottom perimeter edge 224, which defines the fabric opening 226. The oval viewing opening has an adjacent slanted sidewall 232. The vent opening 242 is centrally located on sidewall 216. The switches 294 and 296 are located on sidewall 222 and are positioned centrally and adjacent to sidewall 218. The aforementioned switches 294 and 296 activate the incandescent lamp fixture 260 and the fluorescent lamp fixture 270, in the same manner as shown in FIG. 6.

As shown in FIG. 8, the interior components of housing 212 include the incandescent lamp fixture 260 having a small incandescent light bulb 262 of at least 20 watts received in a porcelain lamp socket 264 and attached to sidewall 252 of storage box 254. Housing 212 also includes fluorescent lamp fixture 270 having a miniature fluorescent light bulb 272 of at least 4 watts received in miniature sockets 274 and 276. One socket 274 is attached to the interior sidewall 216b by a mounting bracket 282, and the other socket 276 is attached to a sidewall 252 of storage compartment 254 by a mounting bracket 284.

The electrical/battery storage compartment 250 has a cover panel 254 secured by holding screws 256 and 258 and includes the switch circuitry for switches 294 and 296; the fluorescent lamp starter and transformer; and the battery source for powering the portable hand-held stain detector apparatus 200. The storage compartment 250 is made of a durable, plastic or metal material.

As shown in FIG. 8, the light reflector 298 is U-shaped and has integrally attached light reflecting sidewalls 300 and 302 and a light reflecting top wall 304 and is located within the interior space of housing 212. Exterior sidewalls 300 and 302 and exterior top wall 304 are adjacent to interior sidewalls 220b and 222b and interior top wall 214b of housing 212, respectively. The light reflector 298 of this second embodiment has an oval opening 314 corresponding to viewing opening 228 and switch openings for switches 294 and 296.

METHOD OF OPERATION OF THE PRESENT INVENTION

The method of operation for the first and second embodiments of the present invention are identical, except for the source of power used in activating and switching ON of stain detectors 10 and 200. Stain detector apparatus 10 uses standard 110 A.C. current via electrical cord 48 for power, whereas the hand-held portable stain detector apparatus 200 uses a battery source for its power needs.

When a customer brings to a dry cleaner a garment to be cleaned and checked for stains, the garment can be examined in a hanging position and/or placed on a spotting board for examination. The stain detector apparatus 10 or 200 is placed on or held next to the garment fabric to be inspected, such that the fabric opening 26 or 226 of housing 12 or 212 faces the stain side of the garment fabric that is under inspection.

The stain detector 10 or 200 is then activated by pressing switch 96 for turning ON the fluorescent lamp 70 or 270 and directing the ultraviolet light rays of the ultraviolet light bulb 72 or 272 toward the fabric opening 26 or 226 and the stain side of the fabric under inspection.

The operator of stain detector 10 or 200 then inspects the stain side of the garment fabric through viewing opening 28 or 228 to determine if any stains are present. The stain detector is moved across the fabric in either an up-and-down or side-to-side sweeping motion or a combination of both, such that the operator of stain detector 10 or 200 has fully inspected the total fabric area for all possible combinations and/or individual stains on the stain side of the fabric.

The operator then determines the type of reaction the ultraviolet light rays have on the stained fabric under inspection. The identification of a particular type of stain on the fabric is made easier for the operator by utilizing a "Stain Detection Analysis Chart Having Recommended Cleaning Methods," as shown below in Table 1 of the present invention.

The chart clearly shows what type of stain under the ultraviolet light rays (and/or the incandescent light rays) provides a particular type of reaction to that type of stain on the fabric. The usual method that a spotter uses to identify stains, without the use of the stain detector of the present invention, is by examining the stain for color, feel, location, shape, and absorption into the garment fabric. The stain detector apparatus 10 or 200 accentuates and highlights the many irregularities of stained areas and, thus, simplifies the process and makes it more accurate.

The operator then turns OFF the ultraviolet light bulb 72 or 272 and lets the stain detector 10 or 200 cool down for 60 to 90 seconds by allowing the heat to dissipate through vent hole 42 or 242. The operator then places fabric opening 26 or 226 on the back side of the stained fabric area and activates the incandescent light 60 or 260 by pressing ON switch 94. The operator then directs the incandescent light rays toward the fabric opening 26 or 226 and on the back side of the stained fabric under inspection.

The operator then inspects the fabric from the stained side while the incandescent light rays are being directed through the fabric from the other side of the stain. The stain detector is moved across the fabric in either an up-and-down or side-to-side sweeping motion, or a combination of both, such that the operator of stain detector 10 or 200 has fully inspected the total fabric area for all possible combinations and/or individual stains previously inspected for on both sides of that garment fabric.

The user then tries to identify the type of stain on the fabric by the type of reaction the incandescent light rays have on the stained fabric under inspection. Again, the identification of a particular type of stain on the fabric under investigation is made easier for the spotter by utilizing the "Stain Detection Analysis Chart," as shown by Table 1, below. Again, the chart clearly shows what type of stain under the incandescent light rays provides a particular type of reaction to that type of stain on the fabric. Also, it should be noted that the incandescent light rays are used to identify flaws in the fabric, such as snagging, shifting of threads in fabric, fabric weak areas, worn-out areas, fabric deterioration due to bleach, fabric beading, and other fabric defects when the fabric is being scanned by the spotter.

For example, if a customer brought in a garment for cleaning, such as a pair of dark-colored slacks, that had multiple unknown stains, the operator would go through the aforementioned procedures to identify the type of reaction the light has on the stains. The operator would then use the "Stain Detection Analysis Chart." If the ultraviolet light on one of the stains showed little or no glow, it would indicate a fresh tannin type of stain (i.e., soft drink) and/or a fresh protein type of stain (i.e., perspiration). When the incandescent light is shown through the above stain, if it gave a brownish and/or dark ring effect, it would indicate that the stain was a fresh tannin stain and not a protein stain. If another stained area reacted with the light to provide a dark reaction with little or no glow under the ultraviolet light, it would indicate an oxidized stain that could be either tannin, protein, and/or an oil type of stain. This would be narrowed down when the incandescent light is shown through the above stain, and if it gave a translucent effect on the stain. This would indicate that the stain was an oxidized oil stain (i.e., butter) and not a tannin or protein stain. The dry cleaner would then use a wet side lubricant and or a fabric acid for the tannin stain removal and a dry side and/or amyl acetate for the oil stain removal.

Thus, the customer benefits by the operator's expertise and knowledge in correctly identifying stains by using stain detector 10 or 200 and the removal of the stains with the proper method thereof. By the dry cleaner using the stain detector of the present invention, they will be able to explain to customers hidden damage and stains that may not be removable. This will avoid claims for improper cleaning by the dry cleaner.

ADVANTAGES OF THE PRESENT INVENTION

Accordingly, the primary advantage of the present invention is that it provides a simple apparatus that allows for stain detection and analysis of fabric flaws in a quick and efficient manner.

Another advantage of the present invention is that it provides a stain detector apparatus that is easily used, lightweight, portable, convenient, and durable.

Another advantage of the present invention is that it provides a stain detector apparatus that is useful to personnel in the areas of textiles, dry cleaners, garment analysts, museum curators, conservators, restorators, and manufacturers and retailers of clothing, textiles, and upholstered furniture.

Another advantage of the present invention is that it provides an easy, simple, and economical method for identifying stains in various types of fabrics.

Another advantage of the present invention is that it provides a method for predetermining fabric defects in various types of fabric materials used in garments, curtains, upholstered furniture, and the like.

It is still another advantage of the present invention in that it provides a method of stain detection that utilizes the effects of light to analyze fabrics, dyes, and stains.

A still further advantage of the present invention is that it provides a stain detector apparatus and method of stain detection that will minimize claim submissions for improper cleaning.

A further advantage of the present invention is that it provides an alternative stain detector apparatus that is battery operated, light weight, compact, portable, and can be hand held.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

TABLE 1

STAIN DETECTION ANALYSIS CHART HAVING RECOMMENDED CLEANING METHODS

| Category of Stains | Ultraviolet/Black Light on Front of Fabric and Stain | Ultraviolet/Black Light on Front of Fabric and Stain | Incandescent Light on Back of Fabric and Stain | Method of Stain Removal from Fabric |
|---|---|---|---|---|
| Tannin stains from vegetable matter, coffee, tea, soft drinks, mustard, soy sauce, etc. | Fresh stains on fabric shows a glow with little or no color effect. | Oxidized stains on fabric shows up dark with little or no glow effect. | Fresh and/or oxidized stains show brown-dark rings effect. | The use of a wet side lubricant, tannin formula, acids for fabrics. |
| Protein stains from living body matter, egg, milk, perspiration, blood, etc. | Same as above. Exception is blood when shown as green or black. | Oxidized stains on fabric shows up dark with little or no glow effect. | Fresh and/or oxidized stains show a white or yellow irregular transparent staining effect. | The use of a wet side lubricant, protein formula, alkali, and digestive stain remover. |
| Oil stains from vegetable petroleum, | Fresh stain on fabric shows a glow effect. | Oxidized stains on fabric shows up dark with | Fresh and/or oxidized stains shows a trans- | The use of a dry side lubricant and amyl acetate. |

TABLE 1-continued

STAIN DETECTION ANALYSIS CHART HAVING RECOMMENDED CLEANING METHODS

| Category of Stains | Ultraviolet/Black Light on Front of Fabric and Stain | Ultraviolet/Black Light on Front of Fabric and Stain | Incandescent Light on Back of Fabric and Stain | Method of Stain Removal from Fabric |
|---|---|---|---|---|
| mineral oil, butter, vegetable oil, cooking oil, soybean, mineral, linseed oils, etc. | | little or no glow effect. | lucent effect on the fabric. | |
| Fluorescent dyes on fabrics increase the optical brighteners used to increase whiteness of an off-white fabric or brightness of a colored fabric. | Fluorescent dye in fabric gives a white or bluish glow on white fabric, and brilliance of colored fabrics enhanced. | Breakdown of fluorescent dye in fabric gives a dull or dark effect. | Attempt Correction<br><br>Wool and silk: removal of stain by the use of an acid, mild oxidizing bleach, or reducing bleach.<br>Cotton, linen, and rayon: removal of stain by the use of an alkali, or mild oxidizing bleach. | |

What is claimed is:

1. A method of detecting and identifying a stain on a fabric having a stain side using a stain detector, wherein said stain detector includes a housing with a fabric opening, a viewing opening, a source of white visible light, a source of ultraviolet light, and an interior reflector, comprising the steps of:

a) placing said housing on the fabric to be inspected, wherein said fabric opening of said housing faces the stain side of the fabric;

b) activating said source of ultraviolet light and directing the ultraviolet light rays toward said fabric opening and the stain side of the fabric;

c) inspecting the stain side of the fabric through said viewing opening to determine if a stain is present;

d) identifying the type of stain by the type of reaction said ultraviolet light rays have on the stain;

e) placing said housing on the fabric to be inspected, wherein said fabric opening of said housing faces the other side of the fabric opposite to the stain side;

f) activating said source of white visible light and directing the white visible light rays toward said fabric opening and said other side of the fabric;

g) inspecting the fabric from the stain side of the fabric to determine if a stain is present; and h) identifying the type of stain by the type of reaction said white visible light rays have on the stain.

2. The method of claim 1, wherein the steps of inspecting the fabric further includes moving said stain detector over the fabric to inspect the fabric.

3. The method of claim 1, wherein the steps of identifying said fabric stain further include using a stain detection chart to identify the type of stain that is on the fabric.

* * * * *